US010493202B2

(12) United States Patent
Hayter

(10) Patent No.: US 10,493,202 B2
(45) Date of Patent: *Dec. 3, 2019

(54) ROBUST CLOSED LOOP CONTROL AND METHODS

(71) Applicant: Abbott Diabetes Care Inc., Alameda, CA (US)

(72) Inventor: Gary Alan Hayter, Oakland, CA (US)

(73) Assignee: Abbott Diabetes Care Inc, Alameda, CA (US)

( * ) Notice: Subject to any disclaimer, the term of this patent is extended or adjusted under 35 U.S.C. 154(b) by 312 days.

This patent is subject to a terminal disclaimer.

(21) Appl. No.: 15/436,986

(22) Filed: Feb. 20, 2017

(65) Prior Publication Data

US 2017/0274144 A1    Sep. 28, 2017

Related U.S. Application Data

(60) Continuation of application No. 14/449,677, filed on Aug. 1, 2014, now Pat. No. 9,572,934, and a continuation of application No. 14/265,065, filed on Apr. 29, 2014, now Pat. No. 9,610,046, which is a continuation of application No. 12/580,915, filed on Oct. 16, 2009, now Pat. No. 8,795,252, which is a continuation of application No. 12/202,305, filed on Aug. 31, 2008, now Pat. No. 8,734,422, which is a
(Continued)

(51) Int. Cl.
*A61M 5/172* (2006.01)
*A61M 5/142* (2006.01)
*A61B 5/145* (2006.01)

(52) U.S. Cl.
CPC ............ *A61M 5/172* (2013.01); *A61M 5/142* (2013.01); *A61M 5/14244* (2013.01); *A61M 5/14276* (2013.01); *A61M 5/1723* (2013.01); *A61B 5/14532* (2013.01); *A61M 2005/14208* (2013.01); *A61M 2205/3523* (2013.01); *A61M 2205/3561* (2013.01)

(58) Field of Classification Search
CPC .... A61B 5/14532; A61M 2005/14208; A61M 2205/3523; A61M 2205/3561; A61M 5/142; A61M 5/14244; A61M 5/14276; A61M 5/172; A61M 5/1723
See application file for complete search history.

(56) References Cited

U.S. PATENT DOCUMENTS 8,795,252 B2 *  8/2014  Hayter ............. A61M 5/14244
                                                600/300
9,572,934 B2 *  2/2017  Hayter ............. A61M 5/14244

* cited by examiner

*Primary Examiner* — Brandy S Lee
(74) *Attorney, Agent, or Firm* — Vorys, Sater, Seymour and Pease LLP

(57) ABSTRACT

Method of monitoring a control operation of a medication delivery system, determining whether a signal level received from an analyte sensor is associated with a fault condition and a potential fault condition, and adjusting a medication delivery rate executed by the control operation when it is determined that the signal level from the analyte sensor is associated with one of the fault condition or the potential fault condition, where the medication delivery rate is adjusted to a first predetermined range when the signal level is associated with the fault condition, and adjusted to a second predetermined range when the signal level is associated with the potential fault condition is provided. Devices, systems and kits for implementing the aforementioned method are also provided.

16 Claims, 12 Drawing Sheets

Related U.S. Application Data division of application No. 12/202,301, filed on Aug. 31, 2008, now abandoned.

ROBUST CLOSED LOOP CONTROL AND METHODS

RELATED APPLICATIONS

The present application is a continuation of U.S. patent application Ser. No. 14/265,065 filed Apr. 29, 2014, now U.S. Pat. No. 9,610,046, which is a continuation of U.S. patent application Ser. No. 12/202,305 filed Aug. 31, 2008, now U.S. Pat. No. 8,734,422, entitled "Closed Loop Control With Improved Alarm Functions"; and is a continuation of U.S. patent application Ser. No. 14/449,677 filed Aug. 1, 2014, now U.S. Pat. No. 9,572,934, which is a continuation of U.S. patent application Ser. No. 12/580,915 filed Oct. 16, 2009, now U.S. Pat. No. 8,795,252, which is a divisional application of U.S. patent application Ser. No. 12/202,301 filed Aug. 31, 2008, now abandoned, entitled "Robust Closed Loop Control and Methods", the disclosures of each of which are incorporated herein by reference for all purposes.

BACKGROUND

Benefits of a closed loop control system for treating diabetic conditions by monitoring glucose levels and adjusting delivery rate of insulin are well known. Such systems, referred to as artificial pancreas, model healthy pancreas which, when functioning normally, produces insulin (by the beta cells (β-cells)) to counteract the rise in glucose levels in the blood stream. As is know, Type-1 diabetes mellitus condition exists when the beta cells in the pancreas either die or are unable to a produce sufficient amount of insulin naturally in response to the elevated glucose levels.

Common treatment of Type-1 diabetes is the use of insulin pumps that are programmed to continuously deliver insulin to the body through an infusion set. The use of insulin pumps to treat Type-2 diabetes (where the beta cells in the pancreas do produce insulin, but an inadequate quantity) is also becoming more prevalent. Such insulin delivery devices are preprogrammed with delivery rates such as basal profiles which are tailored to each user, and configured to provide the needed insulin to the user. Additionally, the preprogrammed delivery rates may be supplemented with periodic administration of bolus dosages of insulin (for example, correction bolus or carbohydrate bolus) as may be needed by the user.

In addition, continuous glucose monitoring systems have been developed to allow real time monitoring of fluctuation in glucose levels. One example is the FreeStyle Navigator® Continuous Glucose Monitoring System available from Abbott Diabetes Care Inc., of Alameda, Calif. The use of such glucose monitoring systems provides the user with real time glucose level information. Using the continuous glucose monitoring system, for example, diabetics are able to determine when insulin is needed to lower glucose levels or when additional glucose is needed to raise the level of glucose.

With the continued rise in the number of diagnosed diabetic conditions, there is on-going research to develop closed loop control systems to automate the insulin delivery based on the real time monitoring of the fluctuation in the glucose levels. Closed loop control algorithms such as, for example, proportional, plus integral, plus derivative (PID) control algorithm or model predictive control algorithm exist and are used to control the automatic delivery of insulin based on the glucose levels monitored. One key concern in such automated systems is safety. For example, the glucose sensor in the closed loop control system may enter failure mode (permanently or temporarily) in which case the monitored glucose level in the closed loop control system will introduce error and potentially result in an undesirable or dangerous amount of insulin being administered. Additionally, the infusion component in the closed loop control system may have errors or experience failure modes that result in an inaccurate amount of insulin delivered to the user.

Indeed, safety considerations as well as accuracy considerations to address and/or minimize the potential unreliability in the components of the closed loop control system are important to provide a robust control system in the treatment of diabetic conditions.

SUMMARY

In one aspect, there is provided a method and device for monitoring a closed loop control operation including signal levels received from an analyte sensor and automatic delivery of medication at least in part in response to the received analyte sensor signals, determining whether the signal level received from the analyte sensor is associated with one of a fault condition or a potential fault condition, and dynamically adjusting a current infusion rate executed by the closed loop control operation when it is determined that the signal level from the analyte sensor is associated with one of the fault condition or potential fault condition, where medication delivery rate is adjusted to a first predetermined range when the signal level is associated with the fault condition, and adjusted to a second predetermined range when the signal level is associated with a potential fault condition, and where the first predetermined range is narrower compared to the second predetermined range.

Also provided are systems and kits.

DETAILED DESCRIPTION

Figure 1:
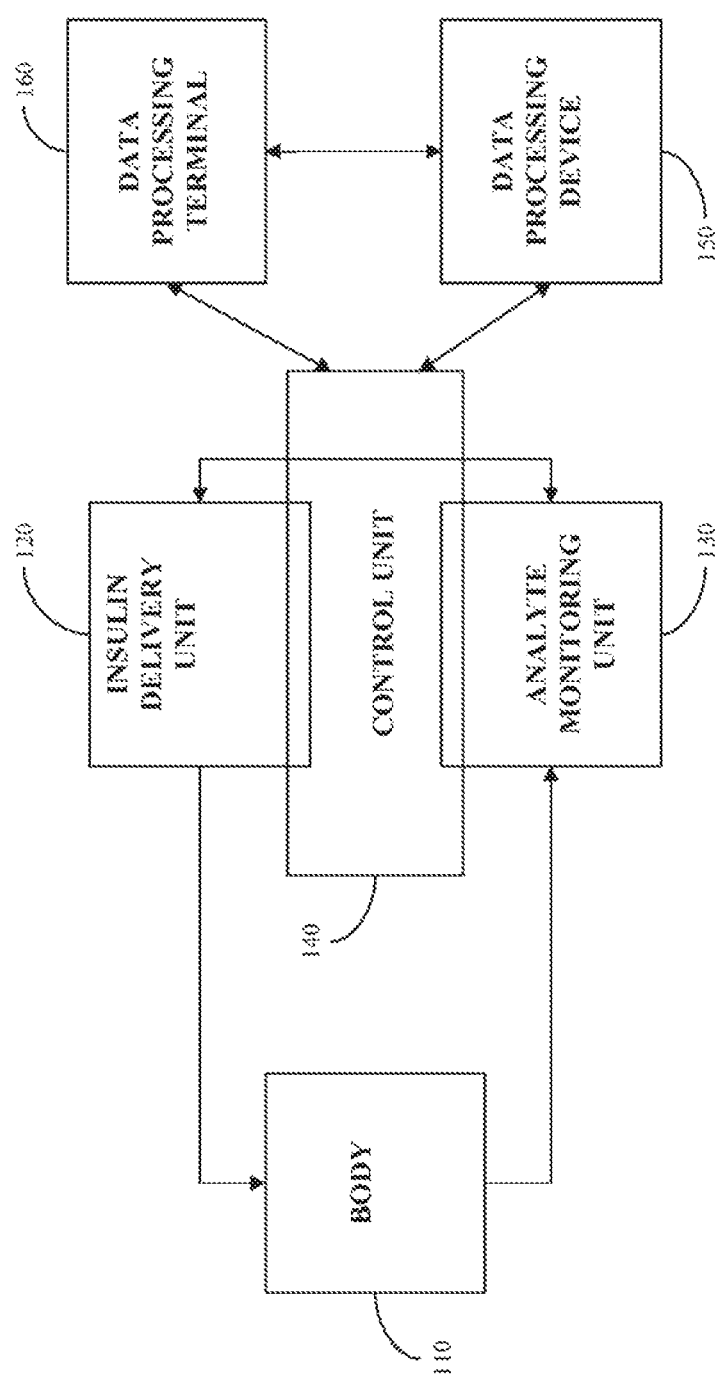
FIG. 1 is a block diagram illustrating an overall closed loop control system in accordance with one embodiment of the present disclosure.

Before embodiments of the present disclosure are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments, of the present disclosure relate to methods and system for a robust closed loop control system with safety parameters for continuously monitoring at least one analyte such as glucose in body fluid and delivering suitable level of medication such as insulin. In certain embodiments, the present disclosure, relates to the continuous and/or automatic in vivo monitoring of the level of an analyte using an analyte sensor, and under the control of a closed loop control algorithm, determining and delivering an appropriate level of medication such as insulin in response to the monitored analyte level.

Embodiments include medication delivery devices such as external infusion pumps, implantable infusion pumps, on-body patch pump, or any other processor controlled medication delivery devices that are in communication with one or more control units which also control the operation of the analyte monitoring devices. The medication delivery devices may include one or more reservoirs or containers to hold the medication for delivery in fluid connection with an infusion set, for example, including an infusion tubing and/or cannula. The cannula may be positioned so that the medication is delivered to the user or patient at a desired location, such as, for example, in the subcutaneous tissue under the skin layer of the user.

Embodiments include analyte monitoring devices and systems that include an analyte sensor—at least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc.

A sensor (and/or sensor insertion apparatus) may be, for example, configured to be positionable in a patient for the continuous or periodic monitoring of a level of an analyte in a patient's dermal fluid. For the purposes of this description, continuous monitoring and periodic monitoring will be used interchangeably, unless noted otherwise.

The analyte level may be correlated and/or converted to analyte levels in blood or other fluids. In certain embodiments, an analyte sensor may be configured to be positioned in contact with dermal fluid to detect the level of glucose, which detected glucose may be used to infer the glucose level in the patient's bloodstream. For example, analyte sensors may be insertable through the skin layer and into the dermal layer under the skin surface at a depth of approximately 3 mm under the skin surface and containing dermal fluid. Embodiments of the analyte sensors of the subject disclosure may be configured for monitoring the level of the analyte over a time period which may range from minutes, hours, days, weeks, months, or longer.

Of interest are analyte sensors, such as glucose sensors, that are capable of in vivo detection of an analyte for about one hour or more, e.g., about a few hours or more, e.g., about a few days of more, e.g., about three days or more, e.g., about five days or more, e.g., about seven days or more, e.g., about several weeks or at least one month. Future analyte levels may be predicted based on information obtained, e.g., the current analyte level at time, the rate of change of the analyte, etc. Predictive alarms may notify the control unit (and/or the user) of predicted analyte levels that may be of concern in advance of the analyte level reaching the future level. This enables the control unit to determine a priori, a suitable corrective action and implement such corrective action.

FIG. 1 is a block diagram illustrating an overall closed loop control system in accordance with one embodiment of the present disclosure. Referring to FIG. 1, in one aspect, the closed loop control system 100 includes an insulin delivery unit 120 that is connected to a body 110 of a user or patient to establish a fluid path to deliver medication such as insulin.

In one aspect, the insulin delivery unit 120 may include an infusion tubing fluidly connecting the reservoir of the delivery unit 120 to the body 110 using a cannula with a portion thereof positioned in the subcutaneous tissue of the body 110.

Referring to FIG. 1, the system 100 also includes an analyte monitoring unit 130 that is configured to monitor the analyte level in the body 110. As shown in FIG. 1, a control unit 140 is provided to control the operation of the insulin delivery unit 120 and the analyte monitoring unit 130. In one embodiment, the control unit 140 may be a processor based control unit having provided therein one or more closed loop control algorithm to control the operation of the analyte monitoring unit 130 and the delivery unit 120. In one aspect, the control unit 140, the analyte monitoring unit 130 and the delivery unit 120 may be integrated in a single housing. In other embodiments, the control unit 140 may be provided in the housing of the delivery unit 120 and configured for communication (wireless or wired) with the analyte monitoring unit 130. In an alternate embodiment, the control unit may be integrated in the housing of the analyte monitoring unit 130 and configured for communication (wireless or wired) with the delivery unit 120. In yet another embodiment, the control unit 140 may be a separate component of the overall system 100 and configured for communication (wireless or wired) with both the delivery unit 120 and the analyte monitoring unit 130.

Referring back to FIG. 1, the analyte monitoring unit 130 may include an analyte sensor that is transcutaneously positioned through a skin layer of the body 110, and in signal communication with a compact data transmitter provided on the skin layer of the body 110 which is configured to transmit the monitored analyte level substantially in real time to the analyte monitoring unit 130 for processing and/or display. In another aspect, the analyte sensor may be wholly implantable in the body 110 with a data transmitter and configured to wirelessly transmit the monitored analyte level to the analyte monitoring unit 130.

Referring still to FIG. 1, also shown in the overall system 100 is a data processing device 150 in the signal communication with the one or more of the control unit 140, delivery unit 120 and the analyte monitoring unit 130. In one aspect, the data processing device 150 may include an optional or supplemental device in the closed loop control system to provide user input/output functions, data storage and processing. Examples of the data processing device 150 include, but are not limited to, mobile telephones, personal digital assistants (PDAs), in vitro blood glucose meters, Blackberry® devices, iPhones, Palm® devices, data paging devices, and the like each of which include an output unit such as one or more of a display, audible and/or vibratory output, and/or an input unit such as a keypad, keyboard, input buttons and the like, and which are configured for communication (wired or wireless) to receive and/or transmit data, and further, which include memory devices such as random access memory, read only memory, volatile and/or non-volatile memory that store data.

Also shown in the overall system 100 is a data processing terminal 160 which may include a personal computer, a server terminal, a laptop computer, a handheld computing device, or other similar computing devices that are configured for data communication (over the internet, local area network (LAN), cellular network and the like) with the one or more of the control unit 140, the delivery unit 120, the analyte monitoring unit 130, or the data processing device 150, to process, analyze, store, archive, and update information.

It is to understand that the analyte monitoring device 130 of FIG. 1 may be configured to monitor a variety of analytes at the same time or at different times. Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same of different times.

Additional detailed descriptions of embodiments of the continuous analyte monitoring device system, calibrations protocols, embodiments of its various components are provided in U.S. Pat. Nos. 6,175,752; 6,284,478; 7,299,082; U.S. patent application Ser. No. 10/745,878 filed Dec. 26, 2003, now U.S. Pat. No. 7,811,231 entitled "Continuous Glucose Monitoring System and Methods of Use", each incorporated by reference in its entirety for all purposes. Additional detailed description of systems including medication delivery units and analyte monitoring devices, embodiments of the various components are provided in U.S. patent application Ser. No. 11/386,915, entitled "Method and System for Providing Integrated Medication Infusion and Analyte Monitoring System" disclosure of which is incorporated by reference for all purposes. Moreover, additional detailed description of medication delivery devices and its components are provided in U.S. Pat. No. 6,916,159, the disclosure of which is incorporated by reference for all purposes.

Referring back to FIG. 1, each of the components shown in the system 100 may be configured to be uniquely identified by one or more of the other components in the system so the communication conflict may be readily resolved between the various components, for example, by exchanging or pre-storing and/or verifying unique device identifiers as part of communication between the devices, by using periodic keep alive signals, or configuration of one or more devices or units in the overall system as a master-slave arrangement with periodic bi-directional communication to confirm integrity of signal communication therebetween.

Further, data communication may be encrypted or encoded (and subsequently decoded by the device or unit receiving the data), or transmitted using public-private keys, to ensure integrity of data exchange. Also, error detection, and/or correction using, for example, cyclic redundancy check (CRC) or techniques may be used to detect and/or correct for errors in signals received and/or transmitted between the devices or units in the system 100. In certain aspects, data communication may be responsive to a command or data request received from another device in the system 100, while some aspects of the overall system 100 may be configured to periodically transmit data without prompting (such as the data transmitter, for example, in the analyte monitoring unit 130 periodically transmitting analyte related signals).

In certain embodiments, the communication between the devices or units in the system 100 may include one or more of a radio frequency (RF) communication protocol, an infrared communication protocol, a Bluetooth® enabled communication protocol, an 802.11x wireless communication protocol, internet connection over a data network or an equivalent wireless communication protocol which would allow secure, wireless communication of several units (for example, per HIPAA requirements) while avoiding potential data collision and interference.

In certain embodiments, data processing device 150, analyte monitoring unit 130 and/or delivery unit 120 may include blood glucose meter functions or capability to receive blood glucose measurements. For example, the housing of these devices may include a strip port to receive a blood glucose test strip with blood sample to determine the blood glucose level. Alternatively, a user input device such as an input button or keypad may be provided to manually enter such information. Still further, upon completion of a blood glucose measurement, the result may be wirelessly and/or automatically transmitted to another device in the system 100. For example, it is desirable to maintain a certain level of water tight seal on the housing of the delivery unit 120 during continuous use by the patient or user. In such case, incorporating a strip port to receive a blood glucose test strip may be undesirable. As such, the blood glucose meter function including the strip port may be integrated in the housing of another one of the devices or units in the system (such as in the analyte monitoring unit 130 and/or data processing device 150). In this case, the result from the blood glucose test, upon completion may be wirelessly transmitted to the delivery unit 120 for storage and further processing.

Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® or Precision® blood glucose test strips from Abbott Diabetes Care Inc. Glucose information obtained by the in vitro glucose testing device may be used for a variety of purposes, computations, etc. For example, the information may be used to calibrate the analyte sensor, confirm results of the sensor to increase the confidence in the accuracy level thereof (e.g., in instances in which information obtained by sensor is employed in therapy related decisions), determine suitable amount of bolus dosage for administration by delivery unit 120.

In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is obtained firstly. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate.

One or more devices or components of the system 100 may include an alarm system that, e.g., based on information from control unit 140, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels reach or exceed a threshold value. An alarm system may also, or alternatively, be activated when the rate of change or acceleration of the rate of change in analyte level increase or decrease, reaches or exceeds a threshold rate of change or acceleration. For example, in the case of glucose monitoring unit 130, an alarm system may be activated if the rate of change in glucose concentration exceeds a threshold value which might indicate that a hyperglycemic or hypoglycemic condition is likely to occur. In the case of the delivery unit 120, alarms may be associated with occlusion conditions, low reservoir conditions, malfunction or anomaly in the fluid delivery and the like. System alarms may also notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Referring yet again to FIG. 1, the control unit 140 of the closed loop control system 100 may include one or more processors such as microprocessors and/or application specific integrated circuits (ASIC), volatile and/or non-volatile memory devices, and additional components that are configured to store and execute one or more closed loop control algorithms to dynamically control the operation of the delivery unit 120 and the analyte monitoring unit 130. The one or more closed loop control algorithms may be stored as a set of instructions in the one or more memory devices and executed by the one or more processors to vary the insulin delivery level based on, for example, glucose level information received from the analyte sensor.

As discussed in further detail below, the one or more control algorithms of the control unit 140 are configured to monitor parameters and conditions associated with a safety indication of the closed loop control system 100 and generate and notify the user, as may be desirable to perform one or more troubleshooting actions and/or automatically revert to a semi-closed loop control mode or a manual control mode that require some level of user, patient or healthcare provider intervention.

Figure 2:
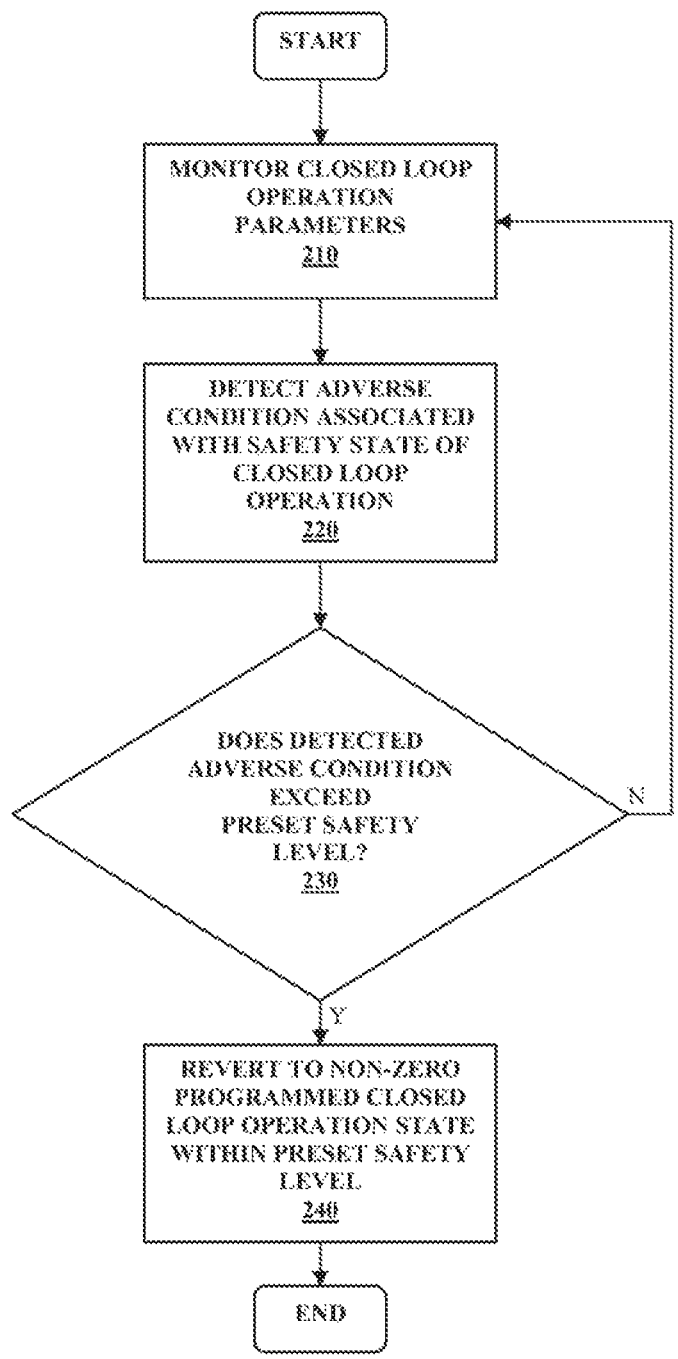
FIG. 2 is a flowchart illustrating adverse condition monitoring and control in a closed loop control system in accordance with one embodiment of the present disclosure.

FIG. 2 is a flowchart illustrating adverse condition monitoring and control in a closed loop control system in accordance with one embodiment of the present disclosure. Referring to FIGS. 1 and 2, in one embodiment, control unit 140 executing the closed loop system control is configured to monitor the closed loop control operation parameters (210). In one aspect, the closed loop control operation parameters may be associated with the operation of the delivery unit 120, and operational conditions associated therewith such as fluid delivery, amount of insulin delivered, potential occlusion and the like. In addition, the closed loop control operation parameters monitored may also include operational conditions associated with the analyte monitoring unit 130 such as, for example, the validity or integrity of analyte sensor signals, unanticipated sensor signal drop out, missing sensor data, and the like. Further, in embodiments where the delivery unit 120 and analyte monitoring unit 130 are separate components in the system 100 communicating via wireless connection, monitored control operation parameters may include the integrity of the communication connection between the devices or units in the system 100.

Referring to FIG. 2, when based on the monitored closed loop operation parameters an adverse condition associated with a safety state of the closed loop operation is detected (220), it is determined whether the detected adverse condition exceeds a preset safety level (230). For example, in the case where the adverse condition is associated with the integrity of analyte sensor signals, it is determined whether a sufficiently accurate glucose level can be derived based on the received sensor signals (for example, based on extrapolation using previously received sensor data, and/or in conjunction with a rate of change of glucose level determination). The adverse condition detected may also include a determined medication delivery level that exceeds a preset threshold level (for example, a physician determined maximum basal delivery rate for the user). As a further example, the adverse condition detected may include communication failure between the components of the overall system 100 including, the analyte monitoring unit 130 and the delivery unit 120.

Referring back to FIG. 2, when it is determined that the detected adverse condition does not exceed a preset safety level, in one aspect, the control unit 140 is configured to proceed with the execution of the closed loop control algorithm based on the real time glucose data received from the analyte monitoring unit 130 to adjust the insulin delivery rate from the delivery unit 120, and the routine returns to monitoring the closed loop operation parameters. On the other hand, if it is determined that the detected adverse condition exceeds the preset safety level, the control unit 140 in one embodiment is configured to command or instruct the delivery unit 120 to revert to a non-zero pre-programmed closed loop operation state within for safety level (240). For example, when it is determined that the determined insulin level for delivery exceeds the safety level or maximum delivery rate (for example, established by a physician or healthcare provider, or the user, and programmed and stored in the control unit 140), the control unit 140 is configured to automatically revert to an insulin delivery rate that is within the safety level so that potential over-dosing may be avoided.

In another aspect, the control unit 140 may be configured to issue a command to the delivery unit 120 every 15 minutes (or some other predetermined time interval) which sets insulin delivery rate for a 20 minute time period (or some other suitable time period). In the event that the adverse condition exceeding the preset safety level is detected preventing the control unit 140 from issuing a new command to the delivery unit 120 during the 20 minute time period, the control unit 140 is configured to instruct the delivery unit 120 to revert to a pre-programmed delivery rate that is within the safety level (for example, a less amount of insulin to be delivered). In a further aspect, the detected adverse condition may include a determination of insulin on board value that, in conjunction with the insulin amount to be delivered, exceeds the upper safety level of insulin delivery, the control unit 140 may be configured to revert to or switch to a preset or pre-programmed level that would bring the insulin delivery amount to be within the determined safety level.

As discussed, in one aspect, the insulin delivery amount that is within the safety level may be pre-programmed in the control unit 140, for example, and implemented as part of the closed loop control to automatically deliver the insulin amount based on the pre-programmed level. In a further aspect, the control unit 140 may be configured to modify or adjust the existing insulin delivery rate that is within the safety level in response to the detected adverse condition (for example, reducing the determined insulin deliver rate by a certain factor such as 75%, to maintain the insulin delivery amount within the safety level).

In this manner, in one aspect, when adverse condition associated with the safety state of the closed loop control operation, the control unit 140 may be configured to operate within a predefined safety range rather than requesting user intervention or disabling the closed loop control operation to revert to a manual control operation mode. While certain examples of adverse conditions are discussed above, within the scope of the present disclosure, any other condition associated with the safety level in the operation of the closed loop control system 100 are contemplated, the detection of any of which initiates the evaluation of the detected condition and appropriate modification to the closed loop control system parameters to continue operation of the closed loop control operation without prematurely disabling the system, while maintaining the desired level of safety in using the closed loop control system 100.

Figure 3:
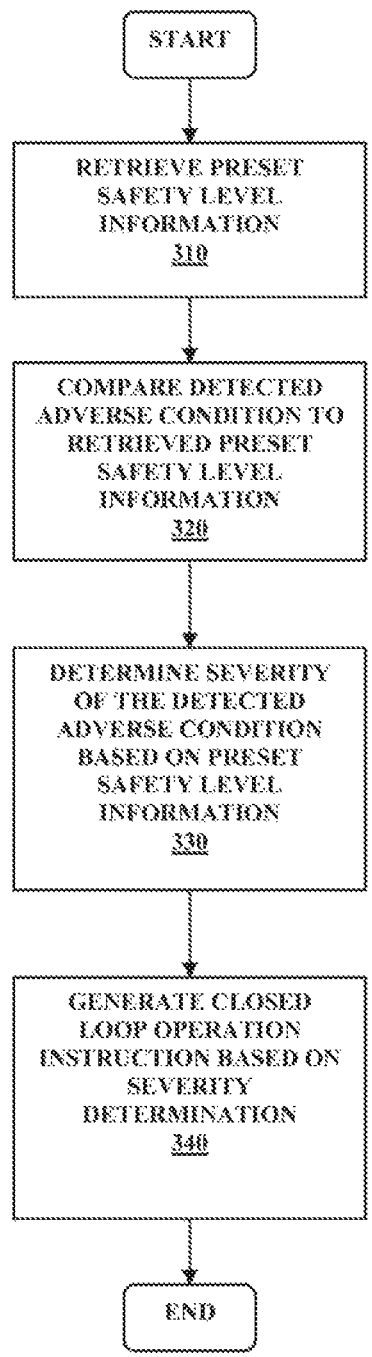
FIG. 3 is a flowchart illustrating adverse condition monitoring and control in a closed loop control system in accordance with another embodiment of the present disclosure.

FIG. 3 is a flowchart illustrating adverse condition monitoring and control in a closed loop control system in accordance with another embodiment of the present disclosure. Referring to FIGS. 1 and 3, in one embodiment, control unit 140 (FIG. 1) retrieves a preset safety level information (310) and compares the retrieved preset safety level information to one or more detected adverse condition (320). Thereafter, a level of severity associated with the detected adverse condition is determined based, at least in part, on the retrieved preset safety level information (330). After determining the severity level, the control unit 140 is configured to generate one or more closed loop operation instructions based on the determined severity level for execution (340).

That is, in one aspect, when an adverse condition is detected by the control unit 140, the control unit 140 (FIG. 1) is configured in one aspect to determine how severe is the detected adverse condition with respect to the automated insulin delivery. For example, control unit 140 may detect a communication failure from the transmitter of the analyte monitoring unit 130 and thus not receive a current sensor data indicative of the glucose level. However, the control unit 140 may have stored in one or more of its memory units previously received glucose levels from the transmitter of the analyte monitoring unit 130. Given an insulin delivery rate that is within the safety level, and a relatively stable glucose value (for example, based on a rate of change of glucose determination from previously received glucose data), the control unit 140 may be configured to declare the communication failure as a non-critical adverse condition detected. In this manner, the generated closed loop operation instruction (340) may not modify the current delivery rate by the delivery unit 120 (FIG. 1).

On the other hand, if the rate of change of the glucose level indicated by previously received sensor data demonstrates a rapid variation in the glucose level, and/or the communication failure persists over a time period that exceeds a certain level (for example, exceeding 20 minutes or some other suitable time frame), the generated closed loop operation instruction (340) may include commands to the delivery unit 120 (FIG. 1) to modify the delivery rate and/or revert to a pre-programmed delivery rate that is within the previously determined safety level. In one aspect, the control unit 140 (FIG. 1) may be configured to continuously monitor the presence of the detected adverse condition until the condition is corrected, in which case, the generated closed loop operation instruction (340) may include commands to the delivery unit 120 to return to the prior closed loop control operation.

Figure 4:
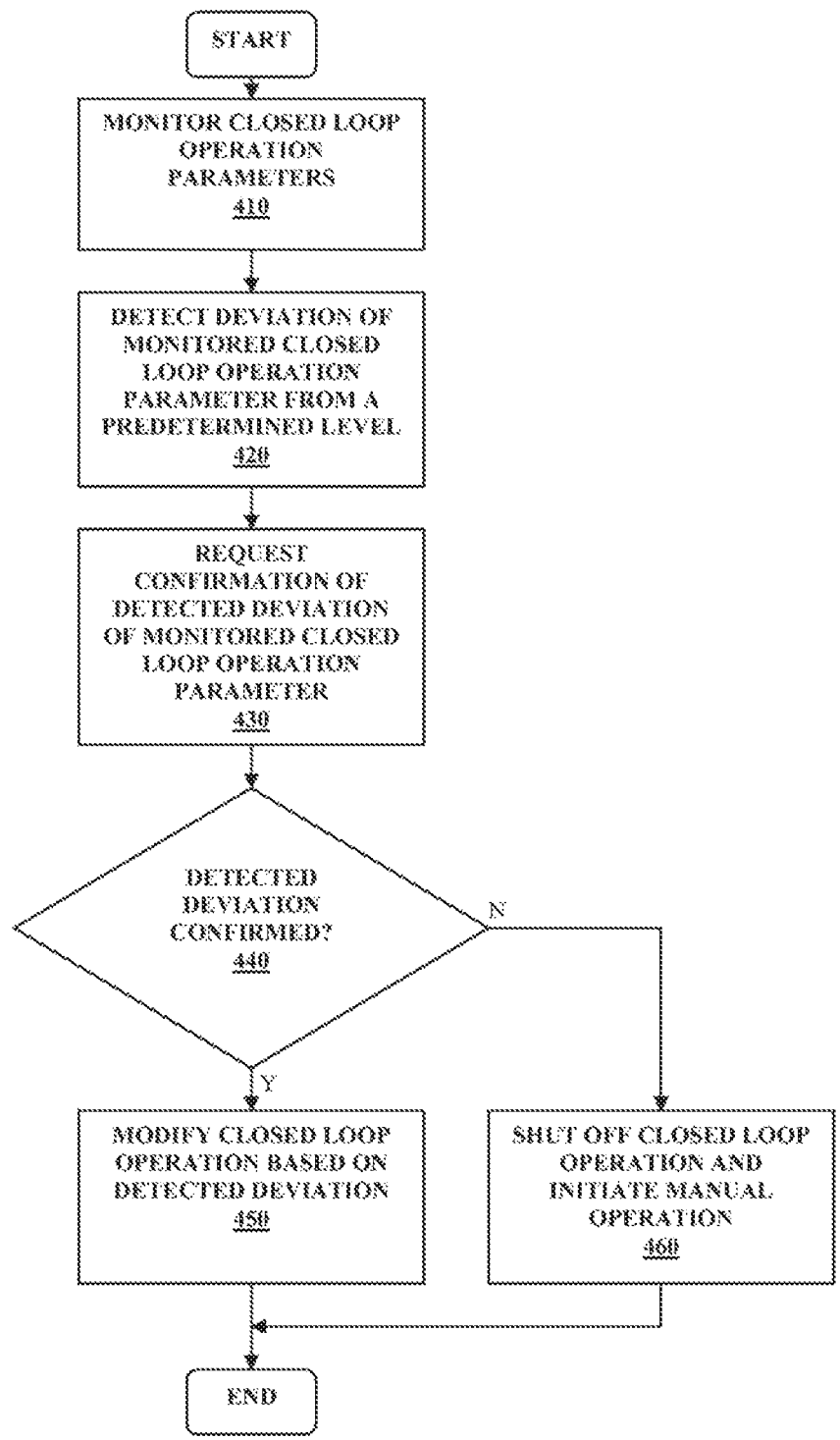
FIG. 4 is a flowchart illustrating condition deviation monitoring and control in a closed loop control system in accordance with one embodiment of the present disclosure.

FIG. 4 is a flowchart illustrating condition deviation monitoring and control in a closed loop control system in accordance with one embodiment of the present disclosure. Referring to FIGS. 1 and 4, in another aspect, control unit 140 (FIG. 1) monitors the closed loop operation parameters (410) and when it detects one or more monitored closed loop operation parameters deviating from a predetermined level (420), the control unit 140 (FIG. 1) may be configured to generate and output a request for confirmation of the detected deviation of the monitored closed loop operation parameter (430).

For example, in the closed loop control system 100 (FIG. 1), a user interface such as a display unit or audible/vibratory notification in the insulin delivery unit 120 and/or the analyte monitoring unit 130 may indicate a notification for the user to confirm the presence of the detected deviation of the monitored closed loop operation parameter. Referring to FIG. 4, if the detected deviation of the monitored closed loop operation parameter is confirmed (440), in one aspect the control unit 140 (FIG. 1) may be configured to modify the closed loop control operation based on the detected deviation of one or more of its parameters (450). On the other hand, if the presence of the detected deviation of the monitored closed loop operation parameter is not confirmed, then the control unit 140 (FIG. 1) may be configured to disable the closed loop control operation, and initiate a manual operation mode (460) to deliver insulin by the delivery unit 120 (FIG. 1).

In this manner, in one aspect, the control unit 140 (FIG. 1) may be configured to request for user confirmation or verification of the presence of the detected adverse condition prior to initiating responsive corrective action, and further, when no verification or confirmation is received, for example, within a set period of time period, the control unit 140 (FIG. 1) may be configured to disable the closed loop control operation. Accordingly, certain adverse conditions detected may prompt the control unit 140 (FIG. 1) to request confirmation prior to automatically responding to such occurrence of adverse condition, and further when no confirmation is received, the control unit 140 (FIG. 1) may temporarily revert to a semi-closed loop or non-closed loop manual delivery mode. In this manner, in certain aspects, a level of safety in using the closed loop control system 100 is maintained, and depending upon the particular detected adverse condition, the control unit 140 may automatically, temporarily adjust the delivery mode of the delivery unit 120 (FIG. 1), or alternatively, require user intervention.

Furthermore, within the scope of the present disclosure, while the detected conditions are described as adverse conditions, any parameter or condition associated with the operation of the closed loop control system 100 are contemplated including but not limited to, analyte sensor operation, sensor signal filtering, sensor signal level, sensor calibration, sensor signal attenuation, communication failure, signal outlier condition, rate of change of the glucose level, insulin delivery rate, insulin on board information, type of insulin, duration of the closed loop control operation, number or frequency of bolus dosage administration, predicted or projected glucose level and/or the direction of the predicted or projected glucose level, frequency of blood glucose measurements, maximum or minimum insulin delivery level, for example.

Figure 5:
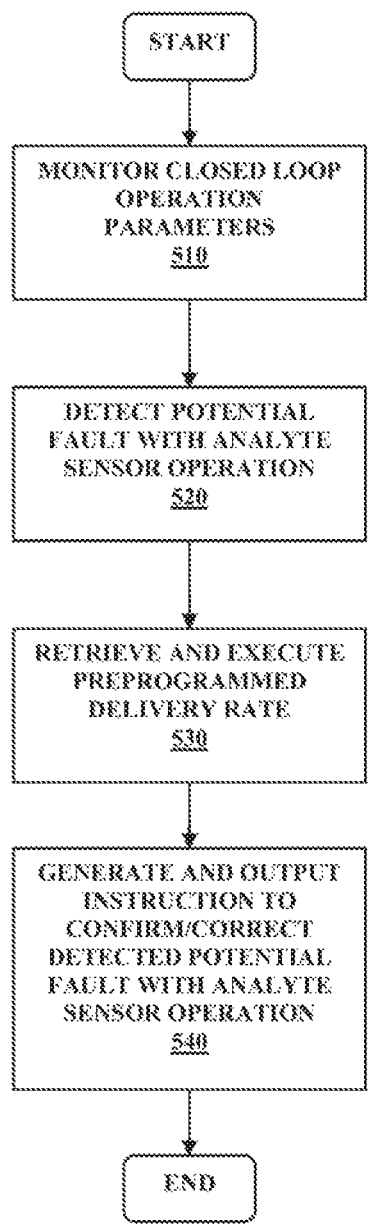
FIG. 5 is a flowchart illustrating analyte sensor condition monitoring and control in a closed loop control system in accordance with one embodiment of the present disclosure.

FIG. 5 is a flowchart illustrating analyte sensor condition monitoring and control in a closed loop control system in accordance with one embodiment of the present disclosure. Referring to FIGS. 1 and 5, in one embodiment control unit (FIG. 1) is configured to monitor closed loop operation parameters (510) in the closed loop control system 100 (FIG. 1). When a potential, fault or failure mode associated with the operation of the analyte sensor is detected (520), the control unit 140 is configured to retrieve and execute a preprogrammed delivery rate (530) (for example, a predetermined, basal profile), while maintaining the closed loop control operation mode. Further, the control unit 140 is configured to generate and output instructions or request to confirm and/or correct the detected potential fault or failure mode of the analyte sensor (540).

That is, in one aspect, the closed loop control operation is not disabled when it is initially detected that the analyte sensor may not be properly functioning. Rather, the closed loop control operation includes the execution of pre-programmed delivery rate that is determined to be within a safety level, and when the potential fault condition or failure mode has been corrected, the control unit 140 may be configured to terminate the execution of the pre-programmed delivery rate and resume real time automatic adjustment to the insulin delivery rate based on the analyte sensor signals.

In this manner, rather than prematurely terminating the operation of the closed loop control system 100 at a first indication of potential failure or fault of the analyte sensor, in one aspect, the control unit 140 is configured to instruct the delivery unit 120 to execute a predetermined delivery rate that is within the safety level until corrective action related to the analyte sensor (for example, replacing the sensor, or recalibrating the sensor with a blood glucose measurement) is performed. In a further aspect, the control unit 140 may be configured to modify the retrieved predetermined delivery rate based on the insulin delivered (for example, to consider the insulin on board level) so that the safety level associated with the amount of insulin to be delivered is maintained.

Figure 6:
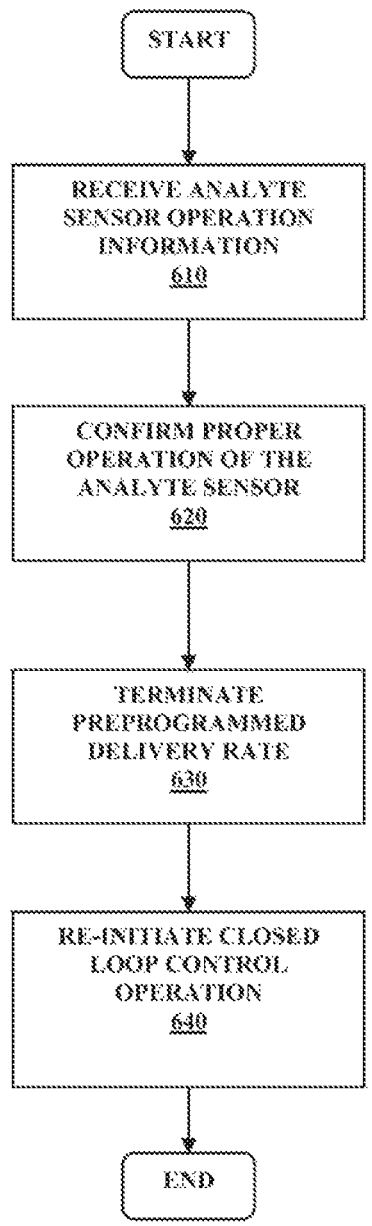
FIG. 6 is a flowchart illustrating analyte sensor condition monitoring and control in a closed loop control system in accordance with another embodiment of the present disclosure.

FIG. 6 is a flowchart illustrating analyte sensor condition monitoring and control in a closed loop control system in accordance with another embodiment of the present disclosure. Referring to FIGS. 1 and 6, in another aspect, when the control unit 140 receives analyte sensor operation information (610), one or more routines are performed to confirm the proper operation for the analyte sensor (620). For example, the control unit 140 may be configured to verify the calibration information of the analyte sensor so that the value level derived therefrom accurately indicates the monitored glucose level.

In a further aspect, the control unit 140 may be configured to retrieve the most recent sensor sensitivity determination based, for example, on the reference blood glucose measurement received, and to compare the retrieved sensitivity to a stored nominal sensitivity for the sensor to confirm a variation between sensitivities not exceeding a predetermined level. In another aspect, when a scheduled calibration event occurs to calibrate the analyte sensor, the current blood glucose measurement is used to determine an updated sensor sensitivity value which may be used in conjunction with one or more prior sensitivity values or nominal sensitivity value.

Referring back to FIG. 6, when it is confirmed that the analyte sensor is in proper operation mode, the preprogrammed delivery rate executed by the delivery unit 120 (FIG. 1) initiated when the sensor potential failure mode was detected, is terminated (630), and the closed loop control operation based on the analyte sensor signals is re-initiated (640).

In the manner described above, in accordance with embodiments of the present disclosure, the operation of the closed loop control system 100 may include monitoring the condition or parameters associated with the analyte monitoring unit 130 and for example, the analyte sensor, and execute one or more routines to instruct the delivery unit 120 to temporarily execute preprogrammed or modified delivery profile determined to be within the safety limits, or to disable the closed loop control operation to maintain the desired degree of safety in using the closed loop control system 100 (FIG. 1). Indeed, in one aspect, for example, when an analyte sensor reading erroneously indicated a high level of glucose which is a false positive value and where the actual glucose level is lower than measured high level of glucose, aspects of the closed loop control operation are configured to establish a limit in the amount of insulin delivered so that when sensor failure is detected, delivery of insulin amount beyond the determined safe level is prevented.

Figure 7:
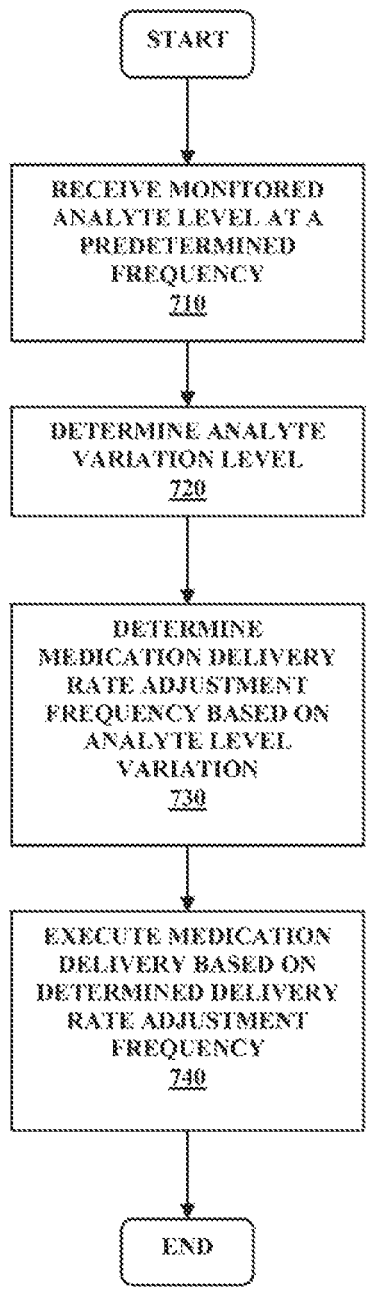
FIG. 7 is a flowchart illustrating variable rate control in a closed loop control system in accordance with one embodiment of the present disclosure.

FIG. 7 is a flowchart illustrating variable rate control in a closed loop control system in accordance with one embodiment of the present disclosure. Referring to FIGS. 1 and 7, in one aspect, control unit 140 executing the closed loop control algorithm in the closed loop control system 100 receives monitored analyte level at a predetermined frequency (710). Based at least in part on the received monitored analyte level, the analyte variation level is determined (720). Thereafter, as shown, the medication delivery rate adjustment frequency is determined based on the determined analyte variation level (730), and thereafter, the delivery unit 120 (FIG. 1) is instructed to deliver the medication at the determined medication delivery rate adjustment frequency (740). That is, in one aspect, the rate of monitored glucose level is associated with the adjustment of the frequency in which to instruct the delivery unit 120 to deliver insulin.

For example, in one aspect, the control unit 140 may be configured to monitor the glucose level from the analyte monitoring unit 130 at a higher frequency (such as, for example once per minute), and also, adjust the rate of insulin delivery by the delivery unit 120 (FIG. 1) at a lower frequency (for example, once every 15 minutes). Indeed, it may be unnecessary to adjust the rate of insulin delivery more frequently than once every 15 minutes when the monitored glucose level (at a higher frequency) does not indicate significant variation in the glucose level. Accordingly, control unit 140 may be configured to issue an instruction or command to the delivery unit 120 once every 15 minutes (or some other suitable interval) to vary the delivery rate based on the glucose level.

One advantage resulting from the less frequent delivery rate adjustment is the conservation of power in the control unit 140 and/or the delivery unit 120. That is, battery power may be conserved by avoiding the generation, communication and/or execution of instructions or commands associated with determining and implementing modification to the insulin delivery rate. On the other hand, since the glucose level is monitored every minute (or at a more frequent time interval), control unit 140 is configured to monitor the variation in the glucose level monitored, and as long as the variation is within a threshold level, the corresponding insulin level delivery adjustment determination is not executed with the same or similar frequency.

However, when the variation in the monitored glucose level exceeds the predetermined threshold level indicating a large variation in the monitored glucose level, or in the cases where a meal event or carbohydrate intake event occurs which will impact the monitored glucose level, it may be desirable to adjust the rate of insulin delivery to be more frequent (for example, adjustment to the delivery rate once every 5 minutes rather than 15 minutes, or with each determination of the glucose level). In this manner, to the extent that adjustment to the insulin delivery rate is desirable, the frequency of the adjustment may be associated with the monitored glucose level such that, for example, control unit 140 may be configured to determine, with each received glucose value, whether adjustment to the insulin delivery rate is needed.

Figure 8:
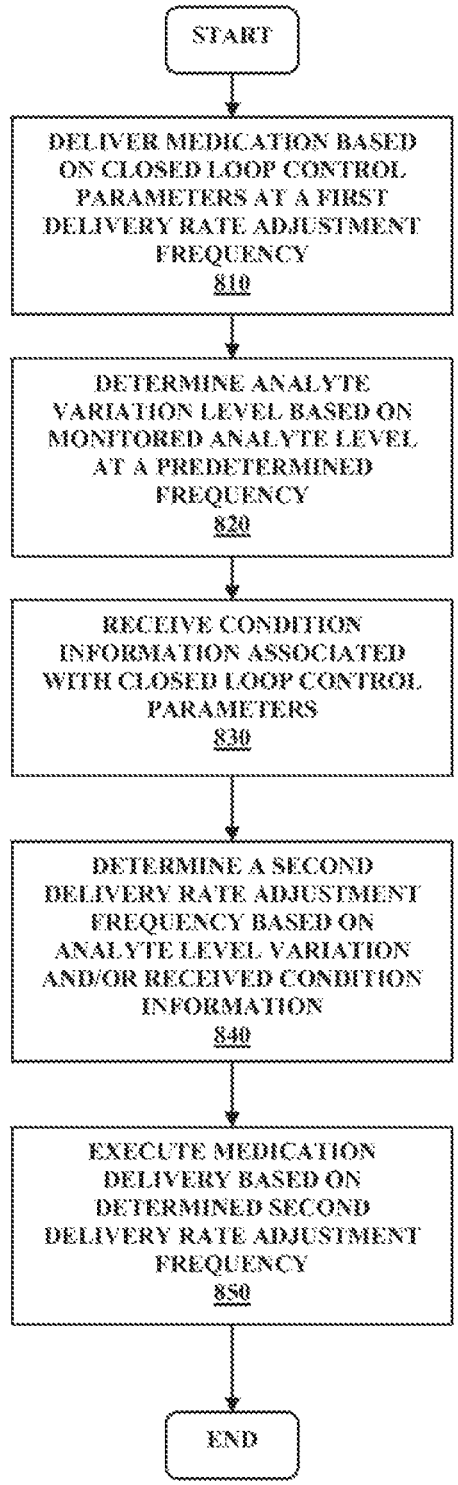
FIG. 8 is a flowchart illustrating variable rate control in a closed loop control system in accordance with another embodiment of the present disclosure.

FIG. 8 is a flowchart illustrating rate control in a closed loop control system in accordance with another embodiment of the present disclosure. Referring to FIGS. 1 and 8, control unit 140 (FIG. 1) in one aspect may be configured to instruct the delivery unit 120 (FIG. 1) to deliver medication based on closed loop control parameters at a first delivery rate adjustment frequency (810). Thereafter, the analyte variation level is determined based on the monitored analyte level at a predetermined frequency (820). Referring back to FIG. 8, one or more condition information (for example, but not limited to an anticipated meal event) associated with the closed loop control parameters is received (830). Thereafter, a second delivery rate adjustment frequency is determined based on the analyte level variation and/or received condition information (840), and the medication delivery is executed (for example, by the insulin delivery unit 120 (FIG. 1) at the determined second delivery rate adjustment frequency (850).

In this manner, in one aspect, control unit 140 is configured to maximize responsiveness to substantial variation in monitored glucose level, or in anticipation of variation in glucose level, while providing lower power requirements for the various components of the system 100 (FIG. 1). Within the scope of the present disclosure, other suitable time intervals or frequency may be used for the glucose monitoring, and further, the associated adjustment to the insulin delivery rate.

That is, embodiments of the present disclosure allow for lower rate of control commands, for example, where the delivery unit 120 and the analyte monitoring unit 130 are configured in the system 100 as separate components, with the control unit 140 provided with the analyte monitoring unit 130 and communicating wirelessly with the delivery unit 120, and each being powered by a respective power supply such as a battery.

Figure 9:
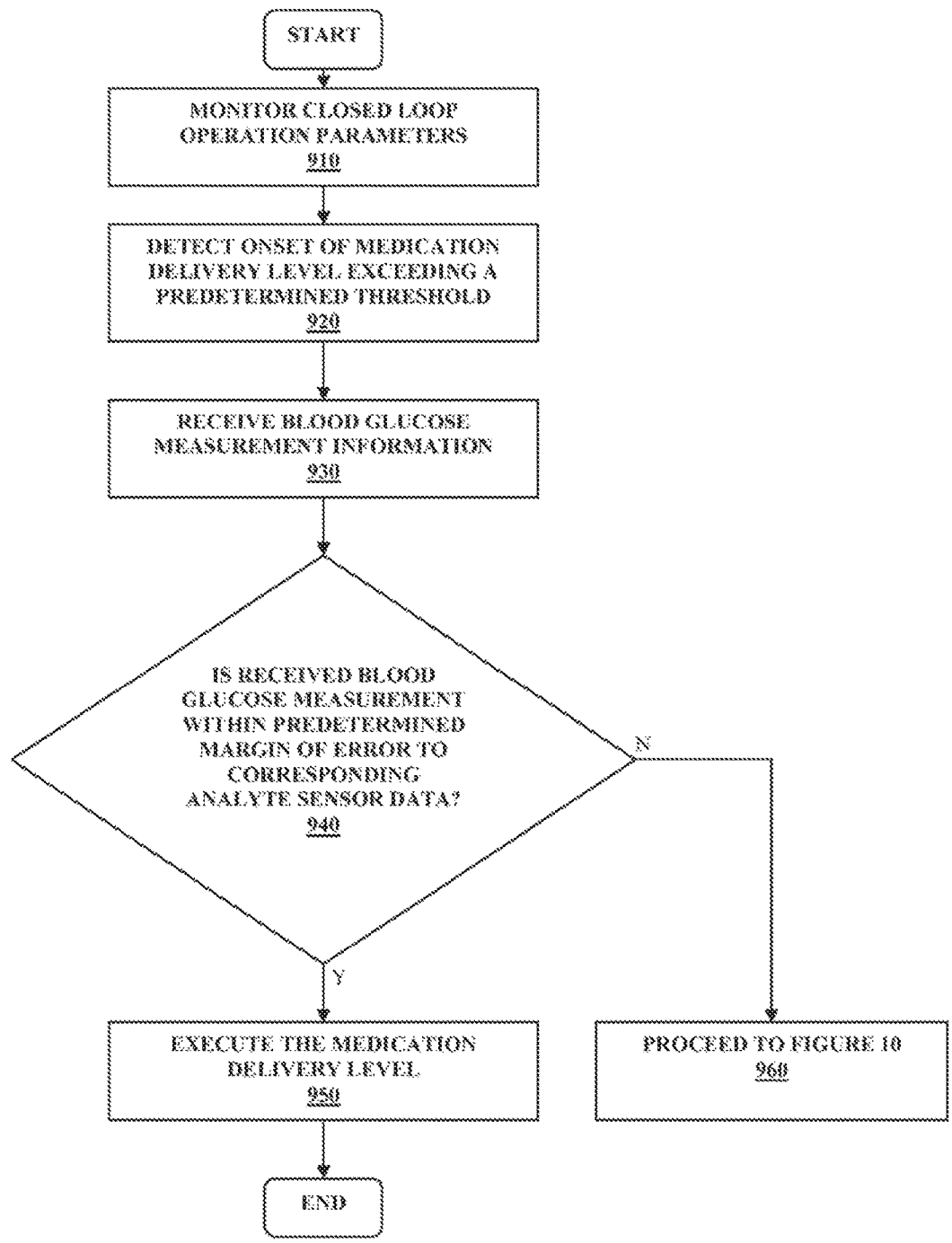
FIGS. 9-10 are flowcharts illustrating blood glucose measurement to improve accuracy of the closed loop control system in accordance with another embodiment of the present disclosure.
Figure 10:
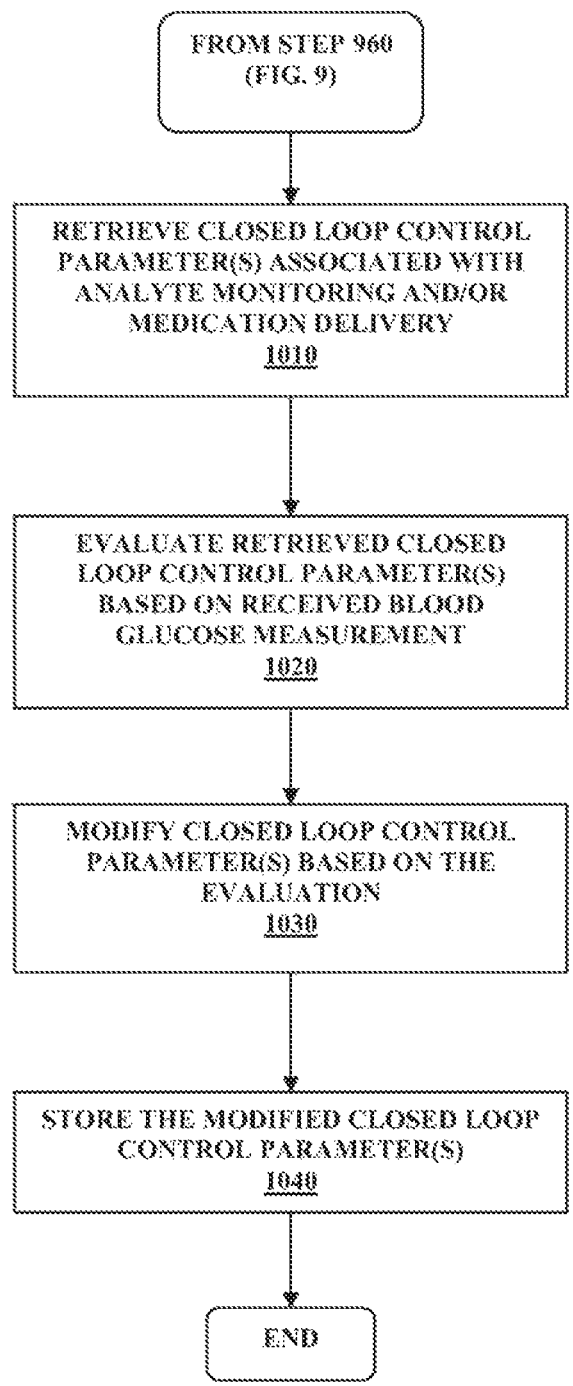

FIGS. 9-10 are flowcharts illustrating blood glucose measurement to improve accuracy of the closed loop control system in accordance with another embodiment of the present disclosure. Referring to FIGS. 1, 9 and 10, closed loop operation parameters are monitored (910) and when onset of medication delivery level (for example, a large insulin dosage level) that exceeds a predetermined threshold level is detected (920) a blood glucose measurement information is received (930) (for example, from a blood glucose meter or manually entered by user input). Based on the received blood glucose measurement information, it is determined whether the received blood glucose measurement is within a predetermined margin of error to a time corresponding analyte sensor data (940). In other words, it is determined whether the sensor data correlates to the blood glucose measurement within a predetermined margin of error.

Referring back to FIG. 9, if it is determined that the analyte sensor data and the blood glucose measurement are within the predetermined margin of error, then the detected onset of medication delivery level is maintained and the delivery unit 120 delivers that level of medication (950). On the other hand, if it is determined that the blood glucose measurement received is not within the predetermined margin of error (940), then referring back to FIG. 9 (960), the closed loop control parameters associated with the analyte monitoring and/or the medication delivery are retrieved (1010), and the retrieved closed loop control parameters are evaluated based on the received blood glucose measurement (1020).

For example, one or more of the closed loop control parameters retrieved may include a request for an additional blood glucose measurement value, an instruction to modify or adjust insulin delivery rate, command to disable closed loop control operation and initiate semi-closed loop control operation or manual control operation, or instruction to recalibrate the analyte sensor, among other. Referring back to FIG. 10, upon evaluation of the retrieved one or more closed loop control parameters, the retrieved one or more parameters may be modified (1030) and thereafter the modified one or more closed loop control parameters is stored (1040).

In this manner, for example, under the control of the control unit 140 (FIG. 1) executing the closed loop control algorithm, when it is detected that a large amount of insulin is to be delivered by the delivery unit 120, the control unit 140, as a safety measure, for example, may prompt the user to enter a current blood glucose measurement (for example, using an in vitro blood glucose meter), to confirm and/or verify the accuracy of the analyte sensor level from the analyte monitoring unit 130 based on which the large amount of insulin to be delivered was determined to execution. For example, a Kalman filter may be used as part of the control unit 140 to process the analyte sensor data and the received blood glucose measurement to optimally adjust the insulin level.

In one aspect, the request or prompt to enter the blood glucose measurement may be initiated when the determined insulin amount for delivery in the closed loop control system 100 exceeds a predetermined safety level established, for example, by a healthcare provider or physician, where the safety level includes, for example, the highest insulin delivery rate without blood glucose measurement confirmation. Within the scope of the present disclosure, other conditions or parameters may be used to trigger the request for blood glucose measurement for confirming sensor accuracy, glucose level verification, and the like.

Further, in another aspect, the control unit 140 may be configured to discontinue requesting blood glucose measurements (even when the insulin level to be delivered exceeds the predetermined safety level) when a predetermined number of successful blood glucose measurement confirmation have occurred and the analyte sensor is considered accurate and stable. Still another aspect of the present disclosure includes modifying the safety level for the highest rate of insulin delivery based on the determination of sensor stability and accuracy in view of, for example, successive confirmation of blood glucose measurements to the corresponding sensor values.

Figure 11:
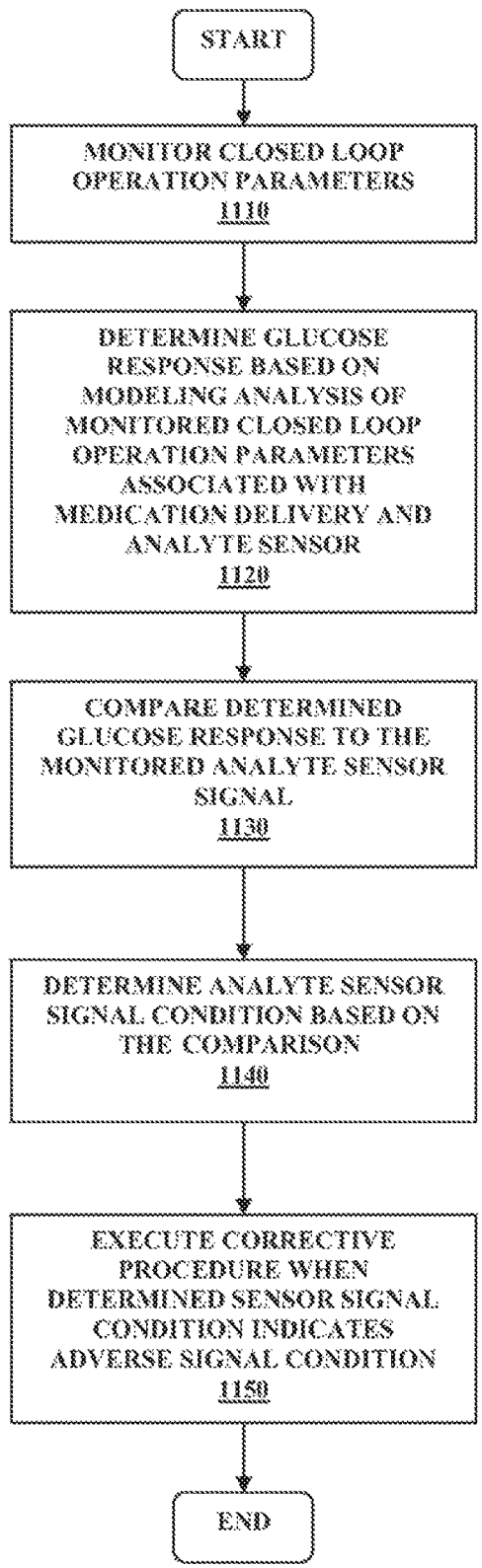
FIG. 11 is a flowchart illustrating medication delivery information to determine analyte sensor condition in a closed loop control system in accordance with one embodiment of the present disclosure.

FIG. 11 is a flowchart illustrating medication delivery information to determine analyte sensor condition in a closed loop control system in accordance with one embodiment of the present disclosure. Referring to FIGS. 1 and 11, in the closed loop control operation state of the closed loop control system 100, control unit 140 (FIG. 1) in one aspect monitors closed loop operation parameters (1110) and performs a predictive modeling analysis of the monitored closed loop control operation parameters associated with the medication delivery and analyte sensor to determine a predictive glucose response (1120). Thereafter, the determined predictive glucose response is compared with the corresponding monitored analyte sensor signal (1130) and a sensor signal condition based on the comparison is determined (1140). For example, based on the comparison, the sensor signal condition may indicate a signal attenuation condition of the glucose sensor. Referring back to FIG. 11, when the sensor signal condition indicates an adverse signal condition or a condition associated with a corrective action or procedure, the corresponding corrective procedure is retrieved and executed by the control unit 140 (1150).

In this manner, in one aspect, using the insulin delivery information, and based on a predictive model implemented to determine a modeled glucose sensor signal, the robustness of the closed loop control system 100 may be enhanced and accuracy of the overall system 100 improved. In one aspect, the predictive model used may include a routine or algorithm that describes glucose response or behavior based on one or more exogenous factors including, among others, insulin delivery information, meal intake, exercise events, and the like, as well as prior monitored sensor data. Accordingly, in one aspect, real time insulin delivery information may be used to improve glucose sensor anomalies such as signal dropouts and early signal attenuation.

For example, as discussed above, the generated modeled glucose sensor response is compared in one aspect to the actual measured sensor data, and based on the comparison, it may be determined that anomalies exist with the glucose sensor. For example, control unit 140 may determine, based on the comparison that sensor signal dropout or early signal attenuation is detected, and thus may prompt the user to enter a reference blood glucose measurement value. In addition, certain alarm or notification functions related to the monitored analyte level such as hypoglycemic alarm, output display of glucose values in real time, may be modified or disabled given the detected anomaly with the sensor signal.

In one aspect, other variables may be compared based on the predictive model and the actual measured sensor signal such as, for example, rate of change of the glucose level determined based on the actual measured values from the sensor and compared with the modeled rate of change information. Additionally, upon determination of the sensor signal drop out or early signal attenuation condition, operations of the analyte monitoring unit 130 may be adjusted accordingly, for example, to mitigate or address the signal abnormality. For example, when such sensor signal condition indicates adverse signal condition at the time of scheduled sensor calibration, the calibration attempt may be disqualified and the user may be instructed to perform another calibration or to delay the calibration until the sensor signal has stabilized and the indicated adverse signal condition is no longer present.

Figure 12:
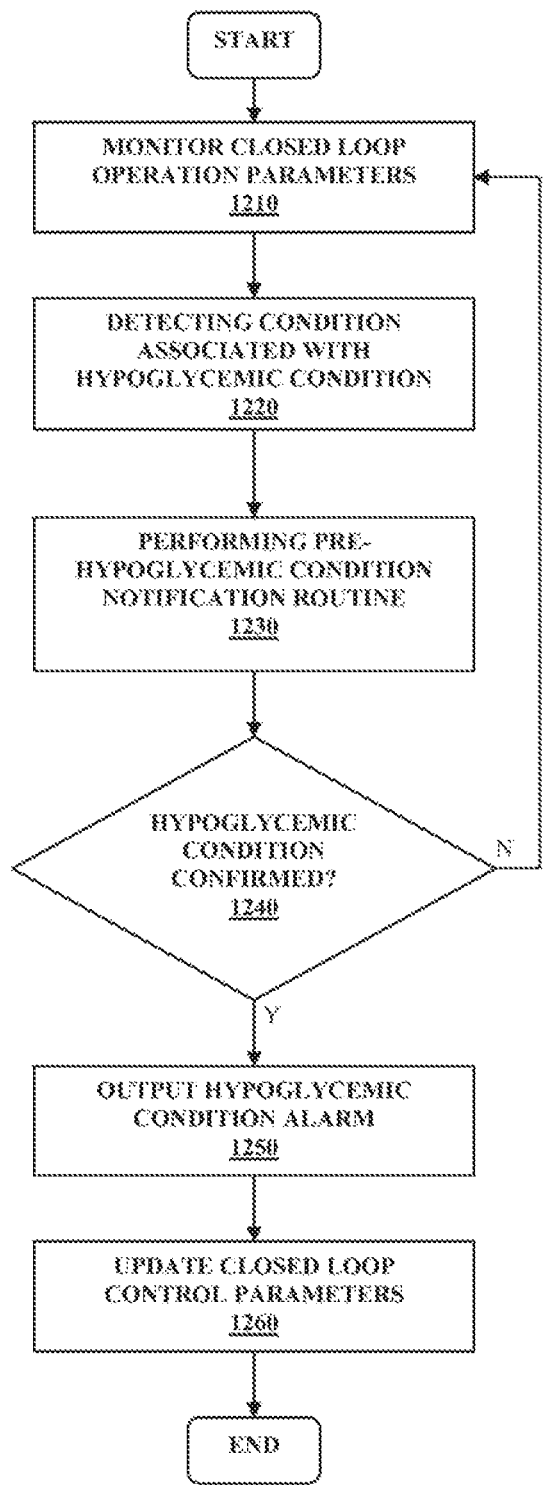
FIG. 12 is a flowchart illustrating detection of false hypoglycemia alarm condition in a closed loop control system in accordance with one embodiment of the present disclosure.

FIG. 12 is a flowchart illustrating detection of false hypoglycemic alarm condition in a closed loop control system in accordance with one embodiment of the present disclosure. Referring to FIGS. 1 and 12, in one aspect, a condition associated with hypoglycemic state is detected (1220) based on monitored closed loop operation parameters (1210) by, for example, the control unit 140 (FIG. 1). Upon detection of the condition associated with the hypoglycemic state, a pre-hypoglycemic condition notification routine is performed (1230). If the hypoglycemic state or condition is confirmed (1240), then a corresponding notification such as a hypoglycemic alarm is output (1250), and the closed loop control parameters are accordingly updated to take into account the detected hypoglycemic condition (1260).

On the other hand, if the hypoglycemic condition is not confirmed (1240), then the routine returns to monitor the closed loop operation parameters (1210). That is, in one aspect, when a condition associated with hypoglycemia is detected, the control unit 140 may be configured to confirm the presence of the detected hypoglycemic state before asserting an alarm notification, for example, to the user. In this manner, potential false hypoglycemic alarms are minimized based on, for example, presence of glucose sensor signal dropout or early signal attenuation or other sensor anomaly state that indicates a false low glucose level.

For example, in accordance with the embodiments of the present disclosure, hypoglycemic alarms or notifications are provided with sensor signal dropout tolerance levels. More specifically, based on the medication delivery rate information, and other parameters associated with the closed loop control operation, the control unit 140 may be configured to determine a degree or level of uncertainty in the measured sensor signal based on the predicted or anticipated glucose level derived, for example, based on the parameters associated with the closed loop control algorithm, including, such as amount of insulin delivered, insulin on board information, glucose rate of change information, among others.

In one aspect, when the onset of a potential hypoglycemic condition is detected, the control unit 140 may be configured to confirm the presence of the hypoglycemic condition, by for example, requiring additional sensor data to be received and analyzed and determining that the sensor signals indicate a persistent low glucose value. In this manner, rather than asserting the hypoglycemic condition notification immediately upon detection of a sensor signal level below the alarm threshold, control unit 140 in one aspect is configured to confirm the presence of the hypoglycemic condition, and upon confirmation, to assert the alarm or notification associated with the hypoglycemic condition.

In another aspect, upon detection of a potential hypoglycemic condition, control unit 140 may be configured to initiate and execute a sensor signal dropout detection algorithm to determine whether the detected potential hypoglycemic condition is associated with sensor signal dropout or attributable to low glucose level. Moreover, in a further aspect, upon detection of the potential hypoglycemic condition, control unit 140 may be configured to assert an alert notification (associated with less urgency or criticality), and if the potential hypoglycemic condition is confirmed, to assert the hypoglycemic condition alarm. For example, the alert notification may include a single audible beep that does not repeat. If the glucose is persistently below the hypoglycemic threshold (or alarm condition level), or below a lower safety threshold, the notification may be escalated to an alarm, for example, with three consecutive audible beeps with or without repeat routines. In this manner, for example, if the sensor signal dropout occurs during night time when the user is asleep, the alert notification may not be loud enough to wake the user, but may be sufficient to cause the user to move or roll over in bed, for example, resulting in the sensor dropout condition being no longer present.

In the manner described, in accordance with the various embodiments of the present disclosure, a robust closed loop control system is provided that includes safety checks and verifications to address potential errors and/or anomalies in detected or monitored conditions and/or parameters enhancing the accuracy and confidence level of the closed loop control operation in the treatment of diabetic conditions.

A method in accordance with one embodiment of the present disclosure includes monitoring a closed loop control operation including signal levels received from an analyte sensor and automatic delivery of medication at least in part in response to the received analyte sensor signals, determining whether the signal level received from the analyte sensor is associated with one of a fault condition or a potential fault condition, dynamically adjusting a current infusion rate executed by the closed loop control operation when it is determined that the signal level from the analyte sensor is associated with one of the fault condition or potential fault condition, where medication delivery rate is adjusted to a first predetermined range when the signal level is associated with the fault conditions, and adjusted to a second predetermined range when the signal level is associated with a potential fault condition, and further, where the first predetermined range is narrower compared to the second predetermined range.

The method may include generating an output signal when the fault condition associated with the analyte sensor is determined based on the signal level, where the output signal may include a command to replace the analyte sensor.

In one aspect, when the potential fault condition is confirmed, the method may include adjusting the medication delivery rate to the first predetermined range.

In another aspect, when the determined fault condition persists over a predetermined time period, the method may include disabling closed loop control operation, and initiating a predetermined medication delivery rate, where the predetermined medication delivery rate may include a pre-programmed basal profile.

The fault condition or potential fault condition may include an early signal attenuation (ESA) condition of the analyte sensor or a signal drop out condition of the sensor.

A method in another embodiment may include monitoring a plurality of parameters associated with a closed loop control operation including continuously monitoring a physiological condition and automatic administration of a medication, detecting an adverse condition associated with the monitored physiological condition or the medication administration deviating from a predetermined safety level of the closed loop control operation, and activating a predetermined safety level threshold for medication delivery such that the level of medication administration in the closed loop control operation does not exceed the predetermined safety level threshold.

The safety level threshold may include a maximum safety limit for insulin administration in the closed loop control operation.

The method may also include deactivating the predetermined safety level threshold when the detected adverse condition is not present.

Further, the method may include modifying the predetermined safety level threshold based, at least in part, on the severity of the detected adverse condition.

Additionally, the method may include outputting a notification to take action in response to the detected adverse condition.

The monitored physiological condition in another aspect may include monitored glucose level, monitored heart rate, monitored exercise level, monitored blood pressure level, or monitored carbohydrate intake level.

The medication may include insulin, or glucagon, or one or more combinations thereof.

In a further aspect, the method may include determining the presence of the adverse condition persistently over a predetermined time period, and disabling the closed loop control operation, and further, also include generating a notification associated with the disabled closed loop control operation.

The method in still another aspect may include initiating a pre-programmed medication delivery rate.

A device in accordance with another embodiment includes one or more processors, and a memory operatively coupled to the one or more processors, the memory for storing instructions which, when executed by the one or more processors, causes the one or more processors to monitor a plurality of parameters associated with a closed loop control operation including continuously monitoring a physiological condition and automatic administration of a medication, detect an adverse condition associated with the monitored physiological condition or the medication administration deviating from a predetermined safety level of the closed loop control operation, and activate a predetermined safety level threshold for medication delivery such that the level of medication administration in the closed loop control operation does not exceed the predetermined safety level threshold.

The safety level threshold may include a maximum safety limit for insulin administration in the closed loop control operation.

The memory for storing instructions which, when executed by the one or more processors, may cause the one or more processors to deactivate the predetermined safety level threshold when the detected adverse condition is not present.

Further, the memory for storing instructions which, when executed by the one or more processors, may cause the one or more processors to modify the predetermined safety level threshold based, at least in part, on the severity of the detected adverse condition.

The memory for storing instructions which, when executed by the one or more processors, may also cause the one or more processors to output a notification to take action in response to the detected adverse condition.

The monitored physiological condition may include monitored glucose level, monitored heart rate, monitored exercise level, monitored blood pressure level, or monitored carbohydrate intake level.

The medication may include insulin, or glucacon, or one or more combinations thereof.

In addition, the memory for storing instructions which, when executed by the one or more processors, may cause the one or more processors to determine the presence of the adverse condition persistently over a predetermined time period, and disable the closed loop control operation.

Also, the memory for storing instructions which, when executed by the one or more processors, may additionally cause the one or more processors to generate a notification associated with the disabled closed loop control operation.

Further, the memory for storing instructions which, when executed by the one or more processors, may cause the one or more processors to initiate a pre-programmed medication delivery rate.

What is claimed is:

1. A method, comprising:
    monitoring a closed loop control operation of a medication delivery system including one or more operation parameters;
    detecting that at least one of the one or more operation parameters deviates from a predetermined threshold;
    prompting a user to confirm the detected deviation from the predetermined threshold;
    adjusting a medication delivery rate based on the detected deviation from the predetermined threshold if the detected deviation is confirmed; and
    disabling the closed loop control operation if the detected deviation is not confirmed.

2. The method of claim 1, wherein said prompting includes one or more of an audio, visual, and/or vibratory stimulus.

3. The method of claim 1, further comprising:
    initiating a predetermined medication delivery rate when the closed loop control operation is disabled.

4. The method of claim 1, wherein the one or more operation parameters include one or more of: an analyte sensor signal level, an analyte sensor calibration, an analyte sensor signal attenuation, an analyte level rate of change, an analyte level direction of change, the medication delivery rate, a medication delivery frequency, a medication delivery level, a medication delivery rate of change, and/or a duration of closed loop control operation.

5. A method, comprising:
    monitoring a closed loop control operation including signal levels received from an analyte sensor and automatic delivery of a medication at least in part in response to the received analyte sensor signal levels;
    detecting that a signal level received from the analyte sensor deviates from a predetermined threshold;
    prompting a user to confirm the detected deviation from the predetermined threshold;
    adjusting a medication delivery rate based on the detected deviation from the predetermined threshold if the detected deviation is confirmed; and
    disabling the closed loop control operation if the detected deviation is not confirmed.

6. The method of claim 5, wherein said prompting includes one or more of an audio, visual, and/or vibratory stimulus.

7. The method of claim 5, further comprising:
    initiating a predetermined medication delivery rate when the closed loop control operation is disabled.

8. The method of claim 7, wherein the predetermined medication delivery rate includes a preprogrammed basal profile.

9. The method of claim 5, further comprising:
    prompting the user to replace the analyte sensor if the detected deviation is confirmed.

10. The method of claim 5, further comprising determining whether the signal level received from the analyte sensor returns to the predetermined threshold.

11. A method, comprising:
    monitoring a closed loop control operation including signal levels received from an analyte sensor and automatic delivery of a medication at least in part in response to the received analyte sensor signal levels;
    detecting that a signal level received from the analyte sensor deviates from a predetermined threshold;
    prompting a user to confirm the detected deviation from the predetermined threshold;
    adjusting a medication delivery rate to a first predetermined range if the detected deviation is confirmed; and
    adjusting the medication delivery rate to a second predetermined range if the detected deviation is not confirmed.

12. The method of claim 11, wherein said prompting includes one or more of an audio, visual, and/or vibratory stimulus.

13. The method of claim 11, further comprising:
    prompting the user to replace the analyte sensor if the deviation is confirmed.

14. The method of claim 11, wherein the second predetermined range includes a preprogrammed basal profile.

15. The method of claim 11, further comprising:
    determining whether the signal level received from the analyte sensor returns to a predetermined threshold.

16. The method of claim 11, wherein the first predetermined range is narrower than the second predetermined range.

* * * * *